United States Patent
Wiktor et al.

(10) Patent No.: US 10,124,103 B2
(45) Date of Patent: Nov. 13, 2018

(54) METHOD FOR OPERATING AN EXTRACORPOREAL BLOOD TREATMENT APPARATUS AND BLOOD TREATMENT APPARATUS

(71) Applicant: Fresenius Medical Care Deutschland GmbH, Bad Homburg (DE)

(72) Inventors: Christoph Wiktor, Gelnhausen (DE); Alexander Heide, Eppstein (DE); Arne Peters, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 208 days.

(21) Appl. No.: 14/903,652

(22) PCT Filed: Jul. 7, 2014

(86) PCT No.: PCT/EP2014/001857
§ 371 (c)(1),
(2) Date: Jan. 8, 2016

(87) PCT Pub. No.: WO2015/003794
PCT Pub. Date: Jan. 15, 2015

(65) Prior Publication Data
US 2016/0166749 A1    Jun. 16, 2016

(30) Foreign Application Priority Data

Jul. 9, 2013   (DE) .................. 10 2013 011 488
Jul. 26, 2013  (DE) .................. 10 2013 012 469

(51) Int. Cl.
*A61M 1/16* (2006.01)
*A61M 1/36* (2006.01)
*A61B 5/00* (2006.01)
*A61B 5/021* (2006.01)
*A61M 1/26* (2006.01)
*A61M 1/10* (2006.01)

(52) U.S. Cl.
CPC ........... *A61M 1/1603* (2014.02); *A61B 5/021* (2013.01); *A61B 5/6866* (2013.01);
(Continued)

(58) Field of Classification Search
CPC .. A61M 1/1603; A61M 1/1005; A61M 1/267; A61M 1/16; A61M 1/3639;
(Continued)

(56) References Cited

U.S. PATENT DOCUMENTS

| 4,293,961 A | 10/1981 | Runge |
| 4,968,422 A | 11/1990 | Runge |

(Continued)

FOREIGN PATENT DOCUMENTS

| CN | 1372479 | 10/2002 |
| CN | 1462343 | 12/2003 |

(Continued)

*Primary Examiner* — Philip R Wiest
(74) *Attorney, Agent, or Firm* — Jacobson Holman, PLLC.

(57) ABSTRACT

The present invention relates to a method for operating an extracorporeal blood treatment apparatus having an extracorporeal blood circuit for a hemodialysis and/or hemofiltration and/or hemodiafiltration by controlling an impeller pump. The invention furthermore comprises that the impeller blood pump is operated in a pulsating manner by adding a pulsating speed portion to a first constant speed.

13 Claims, 2 Drawing Sheets

Figure 1:
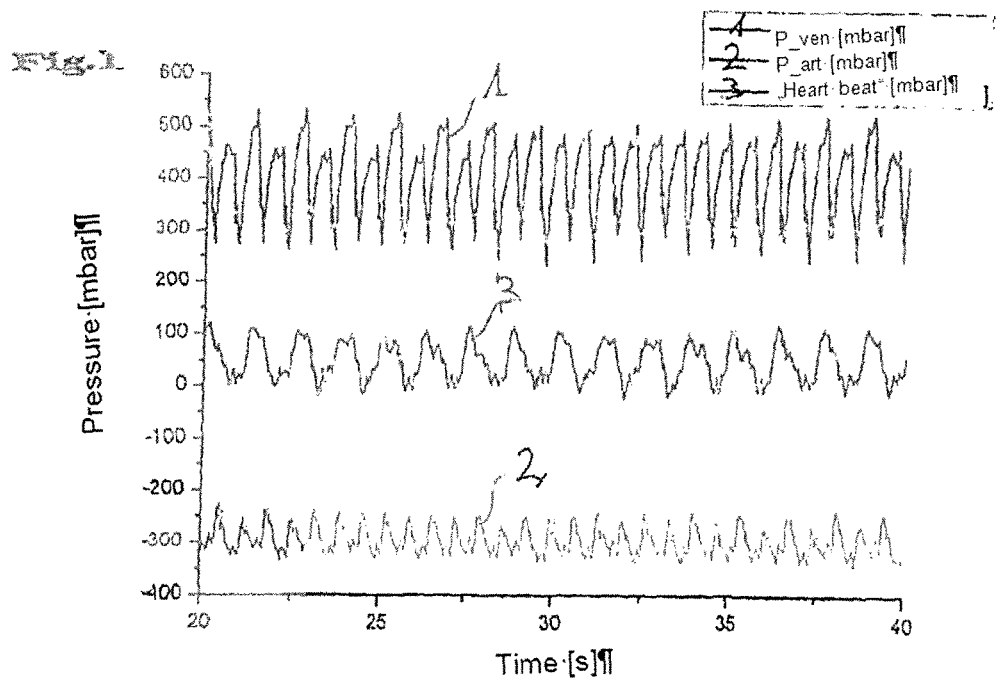

(52) U.S. Cl.
CPC ............ *A61M 1/1005* (2014.02); *A61M 1/16* (2013.01); *A61M 1/267* (2014.02); *A61M 1/3639* (2013.01); *A61M 1/101* (2013.01); *A61M 1/1006* (2014.02); *A61M 1/1086* (2013.01); *A61M 1/3656* (2014.02); *A61M 2205/12* (2013.01); *A61M 2205/3334* (2013.01); *A61M 2205/50* (2013.01); *A61M 2230/005* (2013.01); *A61M 2230/04* (2013.01); *A61M 2230/30* (2013.01)

(58) Field of Classification Search
CPC .. A61M 1/1006; A61M 1/3656; A61M 1/101; A61M 1/1086; A61M 2205/12; A61M 2205/3334; A61M 2205/50; A61B 5/021; A61B 5/6866
USPC ......................................................... 604/6.09
See application file for complete search history.

(56) References Cited

U.S. PATENT DOCUMENTS

| | | | |
|---|---|---|---|
| 5,417,648 | A | 5/1995 | Shibata |
| 7,150,711 | B2 | 12/2006 | Nüsser et al. |
| 8,864,644 | B2 * | 10/2014 | Yomtov ................... A61M 1/10 600/17 |
| 8,956,379 | B2 * | 2/2015 | Luciano ............... A61M 1/1072 604/503 |
| 2005/0101901 | A1 | 5/2005 | Gura |
| 2009/0177279 | A1 | 7/2009 | Luciano et al. |
| 2012/0175295 | A1 * | 7/2012 | Heide ................... A61M 1/101 210/321.63 |
| 2012/0330214 | A1 | 12/2012 | Peters et al. |

FOREIGN PATENT DOCUMENTS

| | | |
|---|---|---|
| CN | 1524000 | 8/2004 |
| CN | 1833736 | 9/2006 |
| CN | 102579238 | 7/2012 |
| DE | 102009060668 | 6/2011 |
| WO | WO 97/10013 | 3/1997 |
| WO | WO 00/64509 | 11/2000 |
| WO | WO 02/24254 | 3/2002 |
| WO | WO 02/064239 | 8/2002 |
| WO | WO 2007/103464 | 9/2007 |
| WO | WO 2011/090927 | 7/2011 |
| WO | WO 2012/095294 | 7/2012 |

* cited by examiner

METHOD FOR OPERATING AN EXTRACORPOREAL BLOOD TREATMENT APPARATUS AND BLOOD TREATMENT APPARATUS

The invention relates to a method for operating an extracorporeal blood treatment apparatus and a corresponding blood treatment apparatus. A method for measuring the pressure pulse waves of a patient's heart, which are caused by cardiac contraction, in the extracorporeal blood circuit of an extracorporeal blood treatment apparatus may especially be used.

It is typically necessary in a hemodialysis treatment, for example, to monitor the heartbeat of the patient. Since direct access to the blood circuit of the patient is already present with the extracorporeal blood circuit, it would be advantageous if the detection of the pressure pulse waves caused by cardiac contraction could take place with the aid of a pressure sensor anyway present at the extracorporeal blood circuit.

In hemodialysis, however, peristaltic blood pumps, which are also called roller pumps or hose pumps, are used as standard for conveying the blood in the extracorporeal blood circuit.

These peristaltic blood pumps, however, impede the measurement of the course of the pressure pulse waves of the patient, which are caused by cardiac contraction, in the extracorporeal blood circuit. The peristaltic blood pumps namely occlude a pump hose segment of the extracorporeal blood circuit by the rollers of their rotor and thus generate a pulsating flow having strong pressure pulses and a pulsating conveying volume stream, It is thus described in detail in WO 97/10013 A1, for example, that occluding hose pumps are typical for hemodialysis in practice and that the pressure pulses of the occluding blood pump cause all other pressure signals in the extracorporeal blood circuit to be drowned out as noise in the unfiltered pressure signal.

Centrifugal blood pumps, which are also called impeller blood pumps, are known outside the field of hemodialysis for other extracorporeal blood circuits, They are used, for example, in heart surgery.

It is further known that such impeller blood pumps can be components of a disposable or of a blood hose kit, in particular also of a blood cassette. The impeller of such an impeller blood pump is as a rule magnetically supported without any direct mechanical coupling—that is contactless—so that the impeller only comes into contact involving friction with the conveyed blood. The support of the impeller can also be a combination of magnetic, hydraulic and/or mechanical support.

It is the object of the present invention to propose an improved method for operating an extracorporeal blood treatment apparatus with an extracorporeal blood circuit in hemodialysis and/or hemofiltration and/or hemodiafiltration by controlling an impeller pump, as well as an improved blood treatment apparatus configured to perform hemodialysis and/or hemofiltration and/or hemodiafiltration with a control and processing unit, which is configured and or programmed to control the impeller blood pump.

This object is achieved in accordance with the present invention by a method in accordance with claim 1 and a blood treatment apparatus in accordance with claim 8.

The present invention provides a method for operating an extracorporeal blood treatment apparatus having an extracorporeal blood circuit for hemodialysis and/or hemofiltration and/or hemodiafiltration by controlling an impeller blood pump. The impeller blood pump is therein operated in a pulsating manner by adding a pulsating speed portion to a first constant speed.

The method in accordance with the invention here makes use of the typical course of the characteristics of impeller blood pumps which allow the controlled provision of a specific pressure pulsation by a pulsating increase in the pump speed above the normal operating point. This property is already shown in DE 10 2009 060 668 A1 and here in particular in FIG. 2 in which the pressure elevation is shown as a function of the blood flow.

It is now hereby possible to provide a pump pulsation without the mean throughflow of the impeller blood pump appreciably differing from a predefined throughflow at a constant speed. A controlled provision of pump pulsations can in turn allow, in accordance with the present invention, an improved operation of the extracorporeal blood circuit using an impeller blood pump.

The pump pulsation may therein especially be specified based on measured pressure pulse waves in the extracorporeal blood circuit, like for example pressure waves of the patient caused by cardiac contraction.

According to the present invention the course of the pressure amplitude can therein be measured at at least one pressure measurement site of the extracorporeal blood circuit. The pump pulsation is therein preferably specified based on this measured course of the pressure amplitude in the extracorporeal blood circuit.

The course of the pressure amplitude may therein especially be measured at at least one pressure measurement site of the extracorporeal blood circuit, wherein the measured course of the pressure amplitude is used as a target value for controlling the pulsating speed portion of the impeller pump. The measured signal of the pressure measurement site may therein be used directly as a target value, for which it may be filtered by a low pass and/or scaled if necessary. The pulsating speed portion may therein be controlled based on the target value and/or controlled by feedback.

The measured course may therein constitute a sum signal of the pressure pulses of the patient's heart reaching the pressure sensor through the arterial and venous patient access. This is due to the fact that no occluding element and especially no occluding pumps are used.

According to the present invention the impeller pump or centrifugal pump may furthermore be located between the pressure sensor and the venous patient access and/or the pressure sensor in the venous drip chamber.

The pulsating operation of the impeller pump may furthermore be synchronized with a course of the pressure pulse waves of the patient in the extracorporeal blood circuit caused by cardiac contraction. A parameter characteristic for the patient's pulse and/or the measured signals mentioned above may especially be used for this purpose.

Based on the operation of the impeller blood pump the pump speed may first be lowered by a specific first speed difference and the pump speed thus reduced may be increased by means of a second speed difference which, however, goes up and down in a pulsating manner at a specific frequency for the synchronization. The blood in the extracorporeal blood circuit can thus be conveyed with a pulsating pressure course synchronously to the heartbeat of the patient.

The mean throughflow of the impeller pump in the extracorporeal blood circuit in this respect remains unchanged (e.g. 500 ml/mm). The removal of blood from the patient access (fistula or shunt or graft) is adapted by the pulsatile, synchronized operation of the impeller pump to the supply of blood in the patient access, i.e. a lot is removed with a large supply and vice versa.

In accordance with a further embodiment of the invention, this synchronization is carried out such that at maximum pressure the blood in the patient access, i.e. in the fistula, is sucked in. It must be taken into account in this respect that it is known that an unwanted fistula circulation of already treated blood can occur in the patient access, which can be applied as a fistula or shunt, if more blood than is available due to the blood flow in the fistula is sucked into the extracorporeal blood circuit by the blood pump via the arterial needle. The missing amount of the blood flow is namely compensated by sucking in the already dialyzed blood led back into the fistula via the venous needle. This in turn has the result of a reduction in the efficiency of the treatment since already dialyzed blood is directly dialyzed again in the extracorporeal blood circuit.

According to the present invention the pulsating operation of the impeller blood pump may therein be synchronized with the course of the pressure pulse waves of the patient in the extracorporeal blood circuit caused by cardiac contraction, such that the fistula circulation of the blood in the extracorporeal blood circuit reaches a minimum.

The method according to the present invention may therein comprise the following steps:
  operating the extracorporeal blood treatment apparatus with the extracorporeal blood circuit for hemodialysis and/or hemofiltration and/or hemodiafiltration, by controlling the impeller blood pump for operation with a constant first speed,
  determining a parameter characteristic for the patient's pulse
  pulsating operation of the impeller blood pump by adding a pulsating speed portion to a first constant speed, wherein the pulsating operation of the impeller blood pump is synchronized with the course of the pressure pulse waves of the patient in the extracorporeal blood circuit caused by cardiac contraction by adding the parameter that is characteristic for the patient's pulse.

The method according to the present invention may furthermore comprise the following steps, which preferably precede the pulsating operation according to the present invention:
  operating the extracorporeal blood treatment apparatus having the extracorporeal blood circuit for hemodialysis and/or hemofiltration and/or hemodiafiltration, by controlling the impeller blood pump for operation with a constant first speed,
  measuring at least one first course of the pressure amplitude at at least one pressure measurement site of the extracorporeal blood circuit and
  extracting the course of at least one pressure pulse wave of the patient caused by cardiac contraction, in the extracorporeal blood circuit from the first course of the measured pressure amplitude.

The course of at least one pressure pulse wave of the patient in the extracorporeal blood circuit caused by cardiac contraction which has thus been extracted may therein be used for controlling the pulsating operation according to the present invention or may be used as the parameter which is characteristic for the patient's pulse.

The extraction of the course of at least one pressure pulse wave of the patient in the extracorporeal blood circuit caused by cardiac contraction from the first course of the measured pressure amplitude according to the present invention does not require an additional step of evaluation. Much rather the course of the measured pressure amplitude may be used directly—if applicable after having been filtered by a low pass and/or scaled—as pressure pulse wave of the patient in the extracorporeal blood circuit caused by cardiac contraction.

Preferably the control of the impeller pump is coupled directly to the measured signal of the pressure sensor, which might be filtered by a low pass against noises, via a control loop. Thus the frequency of the pump modulation is defined directly via the measured signal.

The amplitude of the blood pump modulation may be coupled to the amplitude of the pressure signal with a constant factor, e. g. 1. This factor is preferably saved in the control.

An evaluation of he signal in order to detect certain conditions may thereby be omitted In alternative embodiments other parameters characteristic for the patient's pulse may also be used in addition to or instead of the values of the pressure amplitude measured at at least one pressure measurement site of the extracorporeal blood circuit for the synchronization of the impeller pump or the centrifugal pump. Therefore the parameter characteristic for the patient's pulse may alternatively also be readings from an ECG, heart monitor, blood pressure cuff, ultrasonic measurements and/or flow measurements.

The method according to the present invention may additionally comprise the following steps:
  measuring the transmembrane pressure in the extracorporeal blood treatment apparatus and
  pulsating operation of the impeller blood pump by adding a pulsating speed portion to a first constant speed, wherein the frequency and amplitude of the pulsating operation of the impeller blood pump is set in such a way that the course of the transmembrane pressure follows a predetermined course of the transmembrane pressure.

The transmembrane pressure is the pressure drop via the dialyzer membrane dividing the dialyzator into a blood chamber and a dialysate chamber. According to this aspect of the invention this pressure drop may be influenced specifically by the corresponding operation of the impeller blood pump. It is possible to set a pressure course that is as constant as possible on the one hand or strongly pulsating on the other hand.

The present invention further comprises a blood treatment apparatus configured to perform hemodialysis and I or hemofiltration and/or hemodiafiltration with a control and processing unit, which is configured and/or programmed to control an impeller blood pump. The impeller blood pump is operated in a pulsating manner by adding a pulsating speed portion to a first constant speed. A control and processing unit is especially configured and I or programmed for such an operation.

The control and processing unit may therein be configured and or programmed such that the pump pulsation is controlled based on measured pressure pulse waves in the extracorporeal blood circuit.

The blood treatment apparatus may furthermore comprise a pressure sensor or could be coupled to a pressure sensor, which it uses to measure the course of the pressure amplitude at at least one pressure measurement site of the extracorporeal blood circuit, wherein the measured course of the pressure amplitude is used as a target value for controlling the pulsating speed portion of the impeller pump, wherein the measured signal of the pressure measurement site may be filtered by a low pass and/or scaled if necessary.

The control and processing unit may be configured and/or programmed such that the pulsating operation of the impeller blood pump is synchronized with the course of a pressure pulse wave of the patient in the extracorporeal blood circuit caused by cardiac contraction, especially by using a parameter that is characteristic for the patient's pulse.

Further, the control and processing unit may be configured and/or programmed such that the pulsating operation of the impeller blood pump is synchronized with the course of the pressure pulse waves of the patient in the extracorporeal blood circuit caused by cardiac contraction, such that the fistula circulation of the blood in the extracorporeal blood circuit reaches a minimum.

Further, the control and processing unit may be configured and/or programmed to run the following process:
- operating the extracorporeal blood treatment apparatus having the extracorporeal blood circuit for hemodialysis and/or hemofiltration and or hemodiafiltration by controlling the impeller blood pump for operation at a first constant speed,
- determining a parameter that is characteristic for the patient's pulse
- pulsating operation of the impeller blood pump by adding a pulsating speed portion to a first constant speed, wherein the pulsating operation of the impeller blood pump is synchronized with the course of the pressure pulse waves of the patient in the extracorporeal blood circuit caused by cardiac contraction by using the parameter that is characteristic for the patient's pulse.

Further, the control and processing unit may be configured and/or programmed to run the following process:
- operating the extracorporeal blood treatment apparatus having the extracorporeal blood circuit for a hemodialysis and/or hemofiltration and/or hemodiafiltration by controlling the impeller blood pump for operation at a first constant speed,
- measuring at least a first course of the pressure amplitude at at least one pressure measurement site of the extracorporeal blood circuit and
- extracting the course of at least one pressure pulse wave of the patient's heart in the extracorporeal blood circuit caused by cardiac contraction from the first course of the measured pressure amplitude.

Alternatively the parameter that is characteristic for the patient's pulse may be readings from an ECG, heart monitor, blood pressure cuff, ultrasonic measurements and/or flow measurements. The control and processing unit therein preferably defines at least one of these parameters or has an interface via which at least one of these parameters is provided.

Further, the control and processing unit may be configured and/or programmed to run the following process:
- measuring the transmembrane pressure in the extracorporeal blood treatment apparatus and
- pulsating operation of the impeller blood pump by adding a pulsating speed portion to a first constant speed, wherein for the frequency and amplitude of the pulsating operation of the impeller blood pump is set such that the course of the transmembrane pressure follows a predefined course of the transmembrane pressure.

The blood treatment apparatus according to the present invention may comprise a drive unit for the impeller blood pump, wherein the control and processing unit is configured and or programmed to control and/or regulate the drive unit for the impeller blood pump.

The control and processing unit may furthermore be configured and/or programmed to evaluate the measured signals of the at least one pressure measurement site of the extracorporeal blood circuit.

Preferably the evaluating and/or controlling process is therein conducted automatically by the control and processing unit according to the present invention.

Furthermore the control and processing unit may therein be configured and/or programmed to run one of the above mentioned methods, especially automatically. Furthermore the control and processing unit may be operating as described above with reference to the method.

In a second aspect the present invention comprises—both independently from and in combination with the afore described method or the afore described blood treatment apparatus according to the first aspect—a method for measuring the pressure pulse waves of the patient in the extracorporeal blood circuit of an extracorporeal blood treatment apparatus caused by cardiac contraction comprising the following steps:
- operating an extracorporeal blood treatment apparatus having an extracorporeal blood circuit for hemodialysis and/or hemofiltration and/or hemodiafiltration by controlling an impeller blood pump for operation at a first constant speed,
- measuring at least a first course of the pressure amplitude at at least one pressure measurement site of the extracorporeal blood circuit and
- extracting the course of at least one pressure pulse wave of the patient in the extracorporeal blood circuit caused by cardiac contraction from the first course of the measured pressure amplitude.

The invention makes use of the fact that impeller pumps, and thus also the impeller blood pumps used here, are not occluding and allow pressure pulses to pass without falsification. The pressure pulse waves caused due to the cardiac contraction can thereby be detected very easily.

The impeller blood pump can advantageously be operated in a pulsating manner in a next step following the aforesaid method by adding a pulsating speed portion to a first constant speed. The method in accordance with the invention here makes use of the typical course of the characteristics of impeller blood pumps which allow the direct predefinition of a specific pressure pulsation by a pulsating increase in the pump speed above the normal operating points. This property is already shown in DE 10 2009 060 668 A1 and here in particular in FIG. 2 in which the pressure elevation is shown as a function of the blood flow.

It is now hereby possible, starting from the measured pressure pulse waves in the extracorporeal blood circuit, such as the pressure waves of the patient caused by cardiac contraction, to predefine a pump pulsation without the mean throughflow of the impeller blood pump appreciably differing from the predefined throughflow at a constant speed. A directly predefined pump pulsation can in turn allow, in accordance with the present invention, an improved operation of the extracorporeal blood circuit using an impeller blood pump.

In accordance with a further preferred embodiment, the pulsating operation of the impeller blood pump can be synchronized with the course of the pressure pulse waves of the patient, which are caused by cardiac contraction, in the extracorporeal blood circuit. The synchronization may therein be conducted as explained above with reference to the first aspect described above.

Furthermore the pulsating operation of the impeller blood pump may be synchronized with the course of the pressure pulse waves of the patient in the extracorporeal blood circuit caused by cardiac contraction such that the fistula circulation of the blood in the extracorporeal blood circuit reaches a minimum. Hence, the occurrence of the unwanted fistula circulation can be minimized by a mode of operation of the impeller blood pump synchronized with the course of the pressure pulse waves caused by cardiac contraction.

Finally, the transmembrane pressure in the extracorporeal blood treatment apparatus can advantageously be measured, with the frequency and amplitude being set in a pulsating operation of the impeller blood pump such that the course of the transmembrane pressure follows a predefined course of the transmembrane pressure. The transmembrane pressure is the pressure drop via the dialyzer membrane which dividing the dialyzer into a blood chamber and into a dialysate chamber. This pressure drop can, in accordance with this aspect of the invention, be directly influenced by the corresponding manner of operation of the impeller blood pump. It is possible, on the one hand, to set a pressure course which is as constant as possible, and also a strongly pulsating pressure course, on the other hand.

In alternative embodiments, other parameters characterizing the patient pulse can also be used additionally or instead of the measuring of the pressure amplitude at at least one pressure measurement site of the extracorporeal blood circuit for the synchronization of the impeller pump or of the centrifugal pump. Examples for other parameters characterizing the patient pulse are, for example, measured values from an ECG, heart monitor, blood pressure cuff, ultrasonic measurement, flow measurement and further surrogate parameters for the patient pulse known to the skilled person. The applicant reserves the right to seek protection for such alternative embodiments in potential divisional applications.

In the present patent application, a course of a parameter characterizing the patient flow should be understood as a continuous detection of a measured value of the parameter characterizing the patient pulse or as a phase-wise detection of such a measured value or as a sequential detection of such a measured value, in particular also as repeated individual measurements and measurements " from peak to peak".

In accordance with a further aspect of the invention, a blood treatment apparatus is protected which is configured for carrying out hemodialysis and/or hemofiltration and/or hemodiafiltration. This blood treatment apparatus has, in accordance with the invention, a control and processing unit which is configured and/or programmed to carry out the method of measuring the pressure pulse waves of the patient caused by cardiac contraction, in the extracorporeal blood circuit.

The blood treatment apparatus may comprise a drive unit for the impeller blood pump, wherein the control and processing unit is configured and/or programmed to control and/or regulate the drive unit for the impeller blood pump.

The control and processing unit may furthermore be configured and/or programmed to evaluate the measured signals of the at least one pressure measurement site of the extracorporeal blood circuit.

Figure 2:
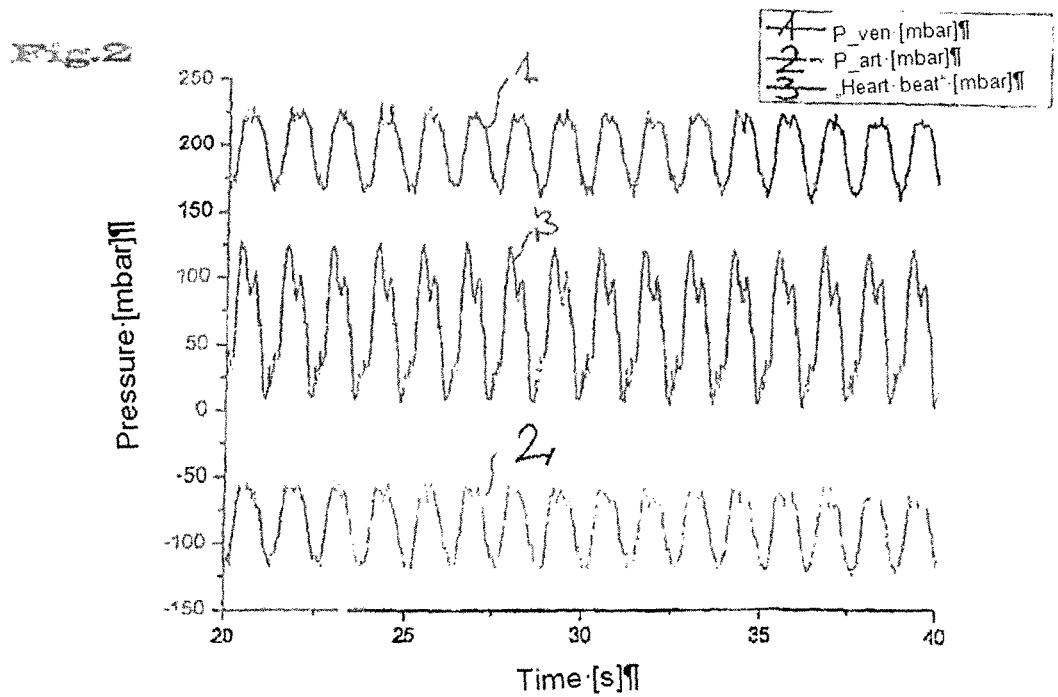
Figure 3:
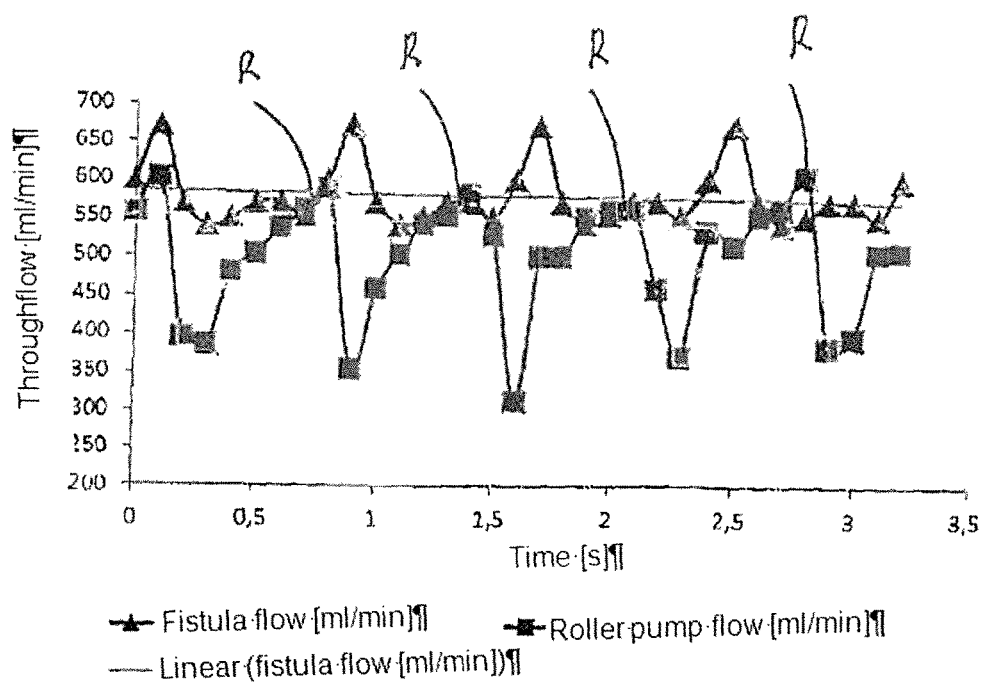
Figure 4:
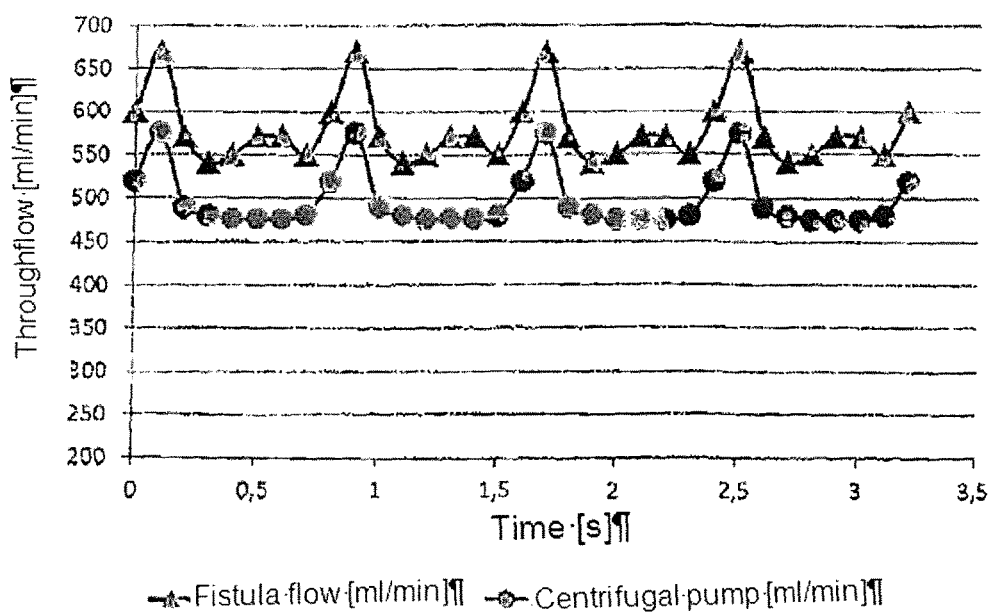

Further features, details and advantages of the invention result from the following description of a preferred embodiment for explaining the pressure pulse waves occurring in the blood circuit in the enclosed Figures. There are shown:

FIG. 1: the measured pressure courses of the venous and arterial pressure course at an extracorporeal blood circuit operated by means of an occluding roller pump, FIG. 2: the measured pressure courses of the venous and arterial blood course at an extracorporeal blood circuit operated by means of an impeller blood pump, FIG. 3: the course of the fistula flow and of the flow of an occluding roller blood pump and FIG. 4: the course of the fistula flow and of the flow of an impeller pump or of a centrifugal pump.

An extracorporeal blood treatment apparatus in accordance with the embodiment corresponds to the design as is described with reference to DE 10 2009 060 668 A. A detailed repetition of this description is dispensed with at this point since it is a standard design.

What is important in the embodiment of the extracorporeal blood treatment apparatus in accordance with the present invention is a control and processing unit and a drive at the machine side for an impeller blood pump. The impeller blood pump comprises a housing with impeller and is preferably a component of the extracorporeal blood hose kit which is particularly advantageously designed as a disposable blood cassette, with the extracorporeal blood hose kit being configured for coupling to the extracorporeal blood treatment apparatus. The blood treatment machine furthermore has at least one pressure sensor which is configured for coupling to a pressure measurement site of the extracorporeal blood hose kit. The pressure sensor and the impeller blood pump are connected to the control and processing unit.

Alternatively—as in the case of integrated RFID pressure sensors at the disposable blood hose kit—a wireless transmission can also be used as a connection to the control and processing unit. At least one arterial pressure measurement site and one venous pressure measurement site are typically present at an extracorporeal blood hose kit. It is, however, not material to the embodiment of the present invention where the at least one pressure sensor is located at the extracorporeal blood hose kit since the amplitude of the measured pressure varies everywhere in the extracorporeal blood circuit due to a heart pressure pulse and can thus be measured at any point of the extracorporeal blood circuit.

The control and processing unit in accordance with the present invention has a data memory in which a computer program is stored. The program code of the computer program is programmed to control the impeller blood pump and to evaluate and store the pressure signals of the at least one pressure sensor.

The operation of the invention can be explained in more detail with reference to the curve course in accordance with FIGS. 1 and 2.

FIG. 1 shows the pressure courses of the venous (curve 1) and of the arterial (curve 2) pressure measured at the extracorporeal circuit, with a conventional peristaltic blood pump being used for operating the extracorporeal blood circuit. The middle curve (marked by 3) shows the corresponding measured pressure course of the pressure pulse from the heart of the patient which was otherwise measured and which is only shown in the same graphic for comparison. It becomes clear here that the strong pressure pulses of the peristaltic pressure pump dominate the pressure signal and greatly falsify it with respect to the amplitude and the frequency. It can be particularly easily recognized with reference to the measured pressure curve of the venous pressure that the pressure pulses of the peristaltic blood pump whose frequency is fixed due to the conveyed blood flow in the extracorporeal blood flow do not necessarily run synchronously with the patient pulse. A beat can also be recognized in the pressure signal. Such a pressure signal is overall not easily suitable to serve as a basis for extracting the course of the pressure pulse waves of the patient caused by cardiac contraction.

The second diagram in accordance with FIG. 2 now shows the measured pressure courses of the venous (curve 1) and of the arterial (curve 2) pressure for the extracorporeal blood circuit which was operated with an impeller blood pump. The middle curve (marked by 3) again shows the corresponding pressure course of the pressure pulse from the heart of the patient which was otherwise measured and which is only shown in the same graphic for comparison. The measured pulses of the arterial and venous pressure measurements here now extend synchronously with those of the measured cardiac pulses. The measured cardiac pulses are not falsified. The course of the pressure pulse waves of the patient which are caused by cardiac contraction can thus be reliably extracted from the arterial and/or venous pressure courses measured at the extracorporeal blood circuit.

FIG. 3 shows by way of example the courses of the fistula flow and of the flow of an occluding roller blood pump in the operation of an extracorporeal blood circuit. The course of the fistula flow has phases of high fistula circulation which are marked by "R". The pulsation frequency of the roller blood pump is inseparably linked to the throughflow which is in turn predefined. The removal of blood from the patient access (fistula or shunt or graft) is therefore not adapted to the pulsatile supply of the blood flow in the patient access.

FIG. 4 shows by way of example the courses of the fistula flow and of the flow of an impeller pump or centrifugal pump in the operation of an extracorporeal blood circuit. The course of the flow of the impeller pump or centrifugal pump takes place at least substantially synchronously with the course of the fistula flow. The synchronization of the pulsation of the impeller pump or of the centrifugal pump can in this respect comprise the pulsation frequency and/or the amplitude of the pulses and can be controlled and/or regulated independently of the predefined mean blood flow in the extracorporeal blood flow. The synchronization can take place with reference to the peak of the patient pulse and/or directly using the measured pressure signals.

The following measuring principle is especially used in the framework of the present invention:

The pressure pulse curve of the heart pulses is measured in the extracorporeal blood circuit (EBC). Since the system according to the present invention does not require any occluding components, and especially no peristaltic pumps, it is intended as an open system, i.e. the pressure pulses of the heart are transmitted to the EBC via both patient ports and are superimposed there. Hence a sum signal is created which is not interfered with by (pressure) actuators of the EBC. Thanks to the system's open concept the pressure sensor may be located at any position in the system and for example a pressure sensor arranged in the venous drip chamber may be used.

Furthermore the impeller pump or a centrifugal pump as opposed to a peristaltic pump does not create its own pressure pulses. Due to the lack of interfering signals from the EBC the sum signal of the signals coming from the patient's heart may therefore be evaluated directly. According to the present invention no post-processing of the signal in terms of a transformation into the frequency domain and/or filtering of signal components, which are based on the pump, is required. The system does not require Fourier transformation.

Therefore the extraction of the course of at least one pressure pulse wave of the patient's heart in the extracorporeal blood circuit caused by cardiac contraction from the first course of the measured pressure amplitude according to the present invention especially does not require an additional step of evaluation. The course of the measured pressure amplitude may rather be used directly—if applicable after filtering by a low pass—as a pressure pulse wave of the patient's heart in the extracorporeal blood circuit caused by cardiac contraction.

An evaluation of the signal in order to detect certain conditions is not conducted.

The control of the impeller pump is coupled directly to the heart pressure pulse signal, which might be filtered by a low pass against noises, via a control loop. Thus the frequency of the pump modulation is controlled directly by the measured signal.

The amplitude of the blood pump modulation may be coupled to the amplitude of the pressure signal with a constant factor, e. g. 1.

The invention claimed is:

1. A method for operating an extracorporeal blood treatment apparatus having an extracorporeal blood circuit by controlling an impeller blood pump,
    characterized in that
    the impeller pump is operated in a pulsating manner by adding a pulsating speed portion to a first constant speed, and the pulsating operation of the impeller pump is synchronized with a course of the pressure pulse waves of the patient's heart in the extracorporeal blood circuit caused by cardiac contraction, by using a parameter which is characteristic for the pulse of the patient.

2. A method according to claim 1, wherein the pump pulsation is controlled in the extracorporeal blood circuit based on measured pressure pulse waves.

3. A method according to claim 1, wherein the course of a pressure amplitude is measured at at least one pressure measurement site of the extracorporeal blood circuit, and wherein the measured course of the pressure amplitude is used as a target value for controlling the pulsating speed portion of the impeller pump, wherein the measured signal of the pressure measurement site is preferably used directly as a target value, for which it might be filtered by a low pass and/or scaled.

4. A method according to claim 1, involving the following steps:
    operating an extracorporeal blood treatment apparatus with the extracorporeal blood circuit, by controlling the impeller blood pump for operation with a constant first speed,
    measuring at least one first course of the pressure amplitude at at least one pressure measurement site of the extracorporeal blood circuit and
    extracting the course of at least one pressure pulse wave of the patient's heart caused by cardiac contraction, in the extracorporeal blood circuit from the first course of the measured pressure amplitude.

5. A method according to claim 1, characterized in that the parameter characterizing the pulse of the patient is a reading from an ECG, heart monitor, blood pressure cuff, ultrasonic measurements and/or flow measurements.

6. A method according to claim 1, comprising the following steps:
    measuring the transmembrane pressure in the extracorporeal blood treatment apparatus and
    pulsating operation of the impeller blood pump by adding a pulsating speed portion to a first constant speed, wherein the frequency and amplitude of the pulsating operation of the impeller blood pump is set such that the transmembrane pressure follows a predetermined course of the transmembrane pressure.

7. A blood treatment apparatus with a control and processing unit, which is configured and/or programmed to control an impeller blood pump,
    characterized in that
    the impeller blood pump is operated by adding a pulsating speed portion to a first constant speed, and the control and processing unit is configured and/or programmed in a way that the pulsating operation of the impeller blood pump is synchronized with a course of the pressure pulse waves of the patient, which are caused by cardiac contraction, in the extracorporeal blood circuit, by using a parameter which is characteristic for the pulse of the patient.

8. A blood treatment apparatus according to claim 7, wherein the control and processing unit is configured and/or programmed to control the pump pulsation on the basis of measured pressure pulse waves in the extracorporeal blood circuit.

9. A blood treatment apparatus according to claim 7, which has a pressure sensor or can be connected to a pressure sensor, which it uses to measure the course of a pressure amplitude at at least one pressure measurement site of the extracorporeal blood circuit, wherein the measured course of the pressure amplitude is used as a target signal for controlling the pulsating speed portion of the impeller pump, wherein the measured signal of the pressure measurement site is preferably used directly as a target value, for which it might he filtered by a low pass and/or scaled.

10. A blood treatment apparatus according to claim 7 characterized in that the control and processing unit is configured and/or programmed to run the following process:
   operating an extracorporeal blood treatment apparatus having an extracorporeal blood circuit by controlling an impeller blood pump for operation at a first constant speed,
   measuring at least one first course of the pressure amplitude at at least one pressure measurement site of the extracorporeal blood circuit and
   extracting the course of at least one pressure pulse wave of the patient's heart, which is caused by cardiac contraction, in the extracorporeal blood circuit from the first course of the measured pressure amplitude.

11. A blood treatment apparatus according to claim 8, wherein the parameter characterizing the pulse of the patient is a reading from an ECG, heart monitor, blood pressure cuff, ultrasonic measurements and/or flow measurements.

12. A blood treatment apparatus according to claim 7, wherein the control and processing unit is configured and/or programmed to run the following process:
   measuring the transmembrane pressure in the extracorporeal blood treatment apparatus and
   pulsating operation of the impeller blood pump by adding a pulsating speed portion to a first constant speed, wherein the pulsating operation of the impeller pump is set by frequency and amplitude such that the course of the transmembrane pressure follows a predefined course of the transmembrane pressure.

13. A blood treatment apparatus according to claim 1, characterized in that it contains the control and processing unit, Wherein the control and processing unit is configured and or programmed to control the drive unit of the impeller pump and/or wherein the control and processing unit is configured and/or programmed to evaluate the measured signals of the at least one pressure measurement site of the extracorporeal blood circuit.

* * * * *